United States Patent [19]

Jeffrey

[11] Patent Number: 5,487,732
[45] Date of Patent: Jan. 30, 1996

[54] SYRINGE WITH RETRACTABLE NEEDLE

[75] Inventor: Peter Jeffrey, Liverpool, Great Britain

[73] Assignee: Safe-T-Limited, Isle of Man, United Kingdom

[21] Appl. No.: 335,795

[22] PCT Filed: May 17, 1993

[86] PCT No.: PCT/GB93/01004

§ 371 Date: Dec. 13, 1994

§ 102(e) Date: Dec. 13, 1994

[87] PCT Pub. No.: WO93/23098

PCT Pub. Date: Nov. 25, 1993

[30] Foreign Application Priority Data

May 15, 1992 [GB] United Kingdom ............ 9210463
Jul. 8, 1992 [GB] United Kingdom ............ 9214512

[51] Int. Cl.⁶ .................................................. A61M 5/00
[52] U.S. Cl. ........................ 604/110; 604/195; 604/218
[58] Field of Search ............................. 604/110, 187, 604/192, 195, 198, 263, 218

[56] References Cited

U.S. PATENT DOCUMENTS 5,019,043  5/1991  Pastor et al. ............... 604/195 X
5,092,853  3/1992  Couvertier, II ............... 604/195
5,120,310  6/1992  Shaw ........................ 604/110

Primary Examiner—John D. Yasko
Attorney, Agent, or Firm—Fitch, Even, Tabin & Flannery

[57] ABSTRACT

A syringe device for cartridged drugs has automatic needle retraction after cartridge contents expression. A drug cartridge is at least partially accommodated within a hollow piston actuator or carrier and is released for further retraction under bias thereinto by way of a piston rod. The piston rod serves to operate a piston contained in the drug cartridge and has deflectable locking arms that extend sideways into latching engagement with a holding formation of the piston actuator. Release of the arms by engagement with the open rear end of the cartridge permits retraction of needle and cartridge. Automatic needle insertion and cartridge contends discharge is also foreseen.

16 Claims, 6 Drawing Sheets

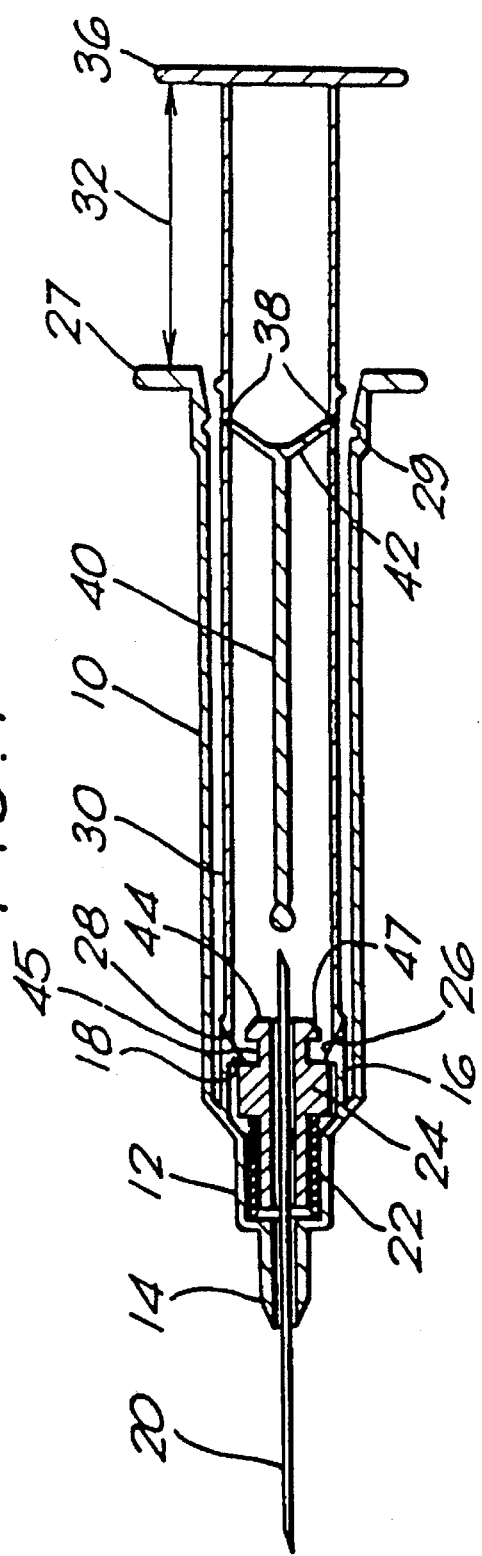
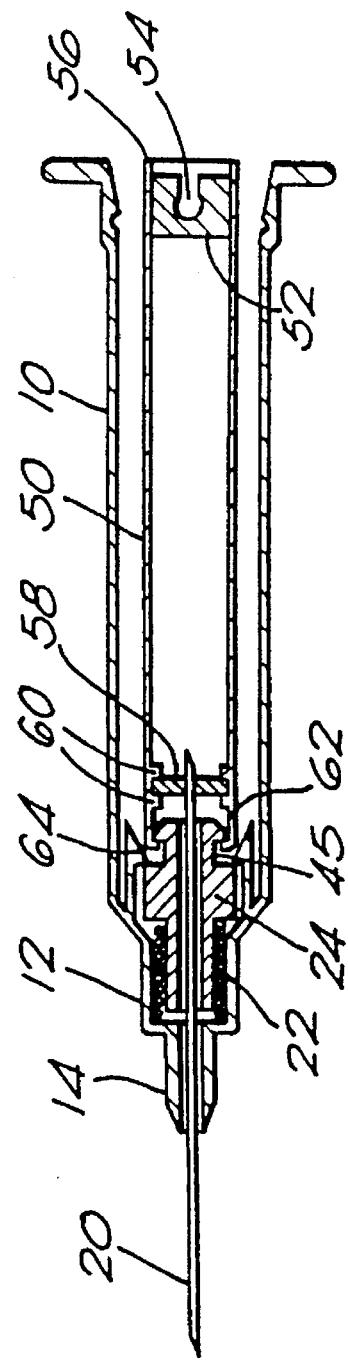
FIG. 1
FIG. 2

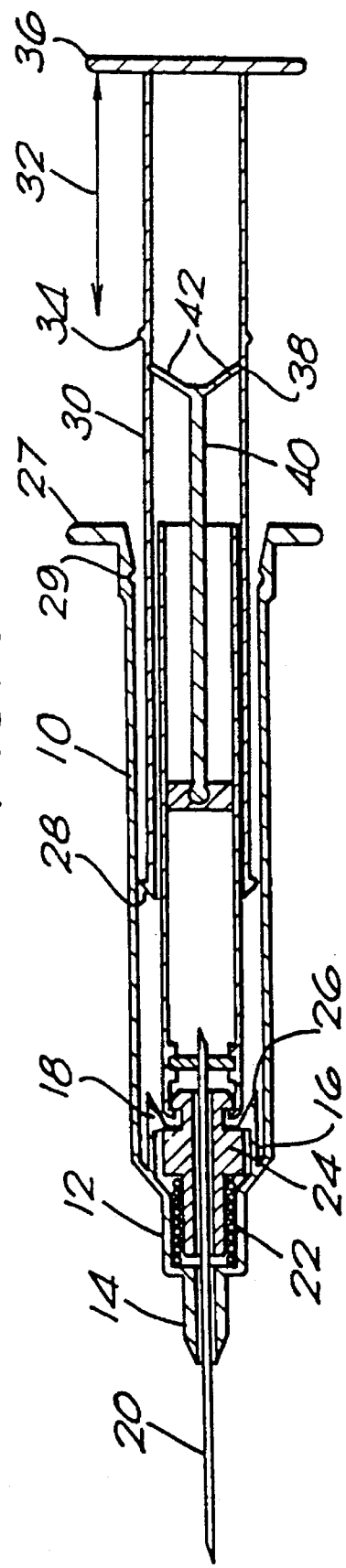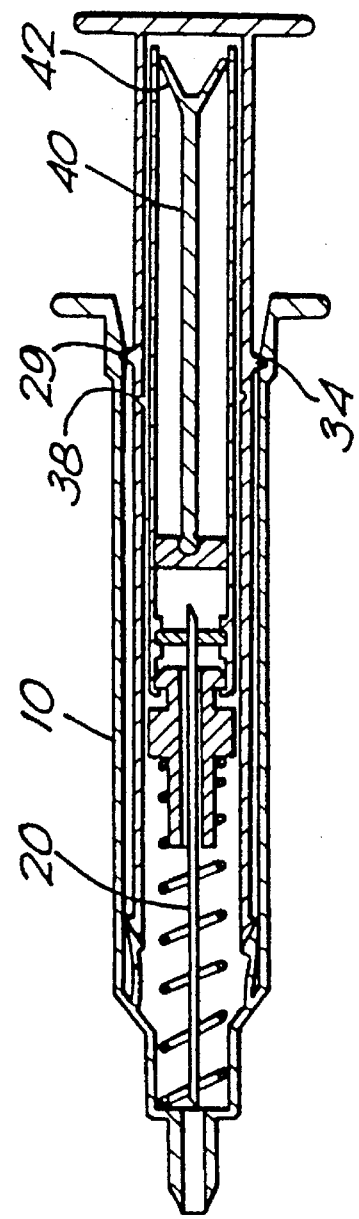

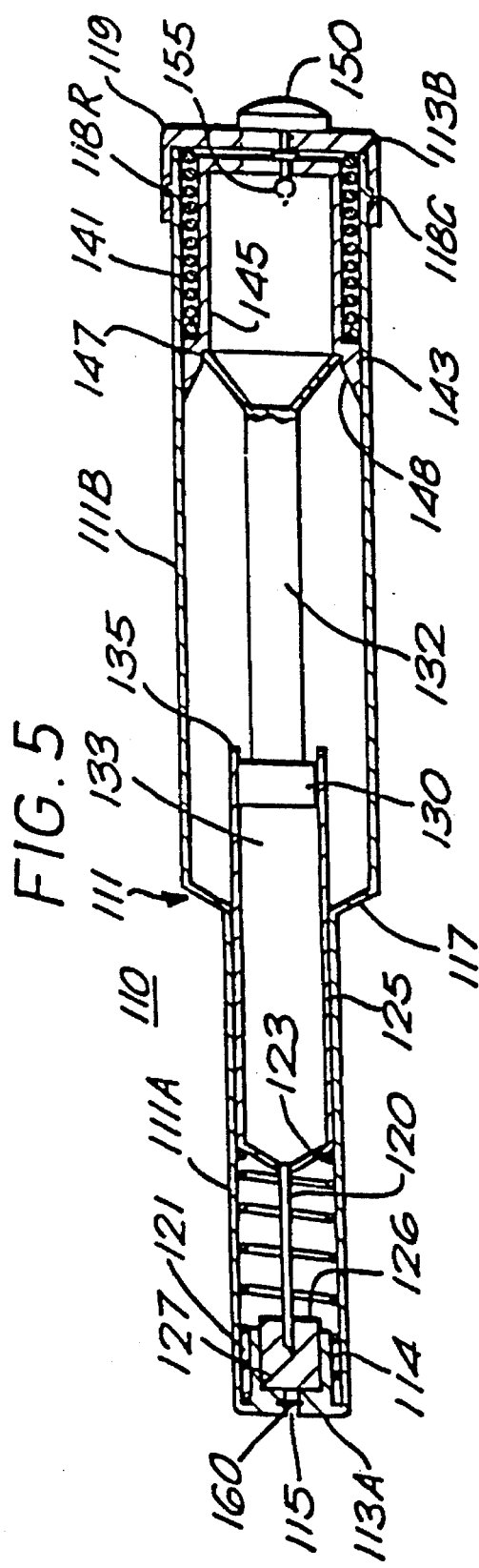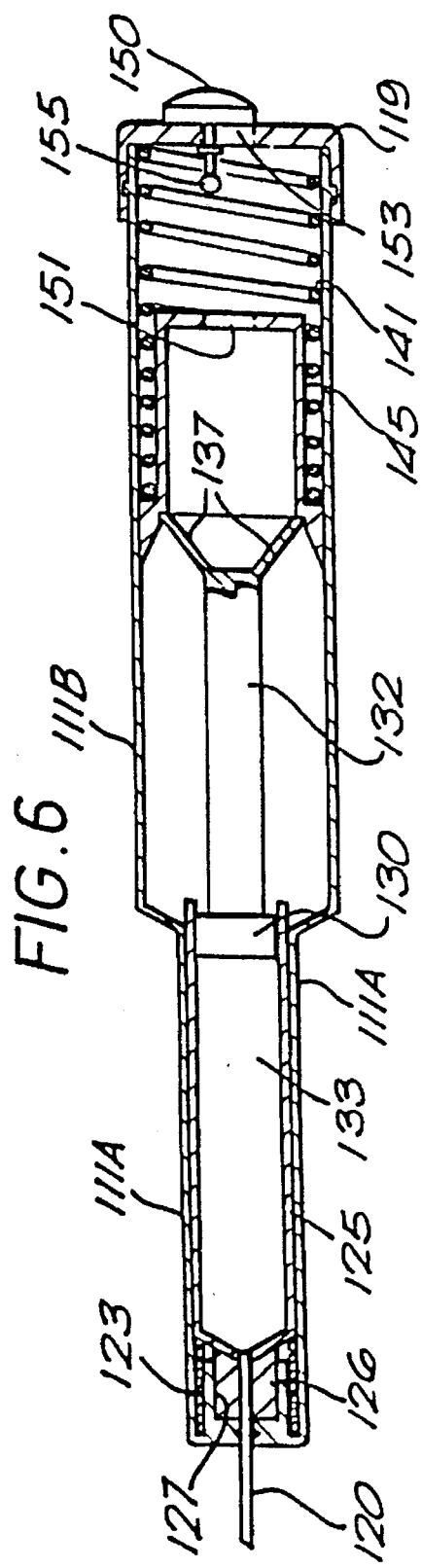

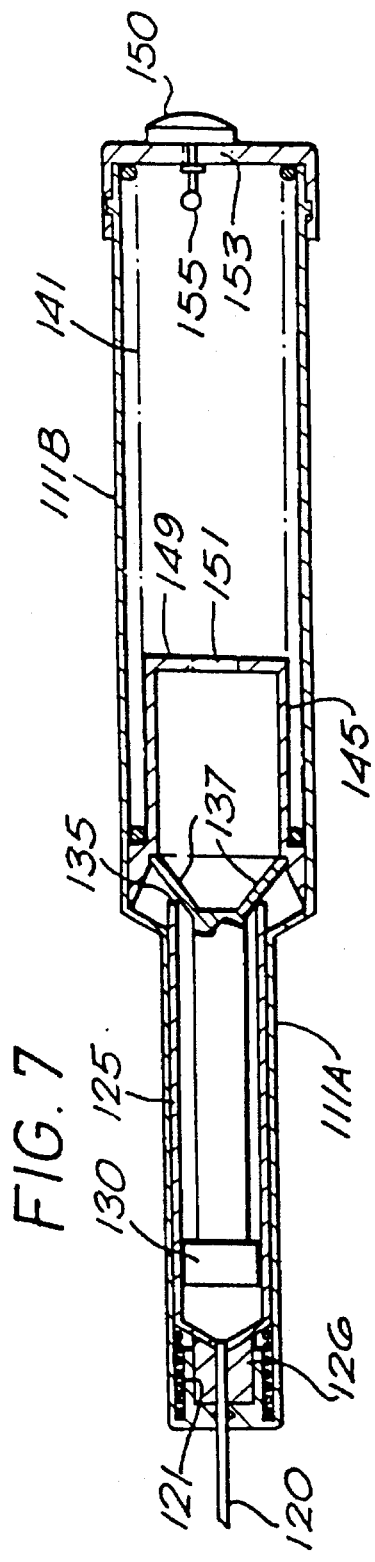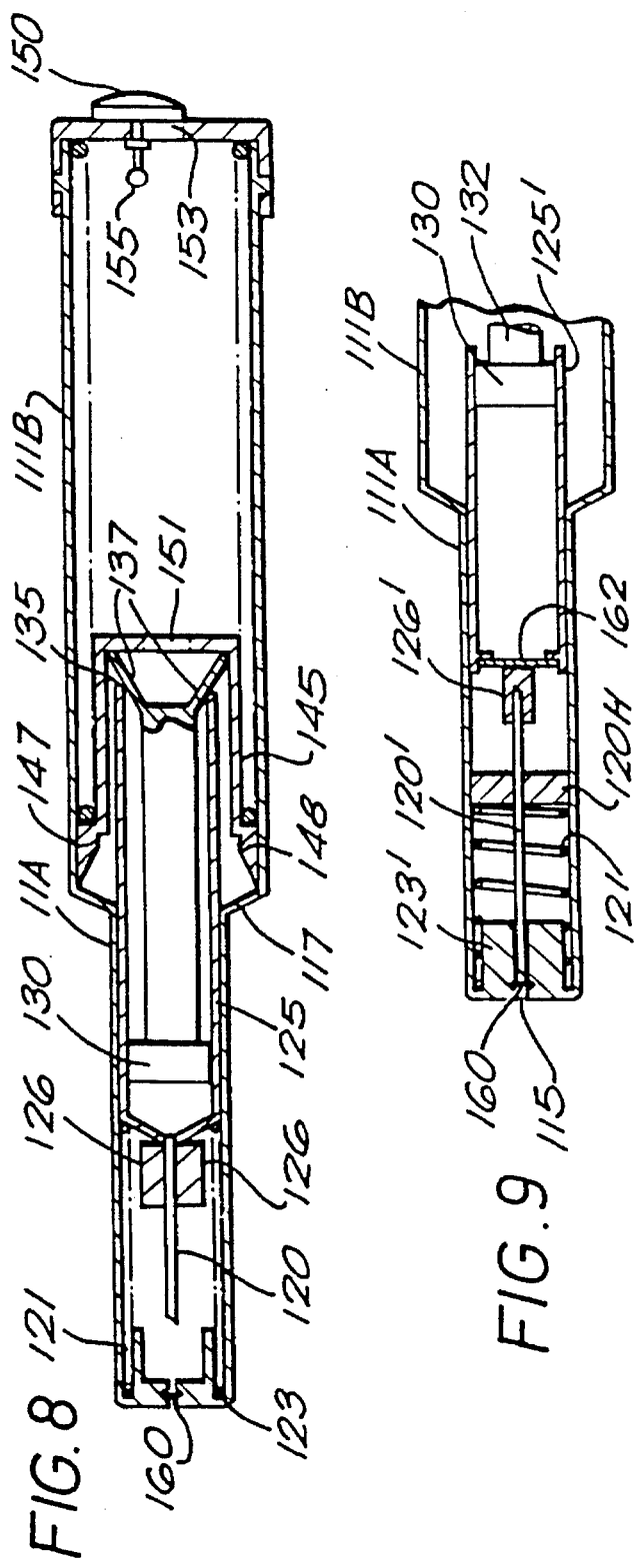

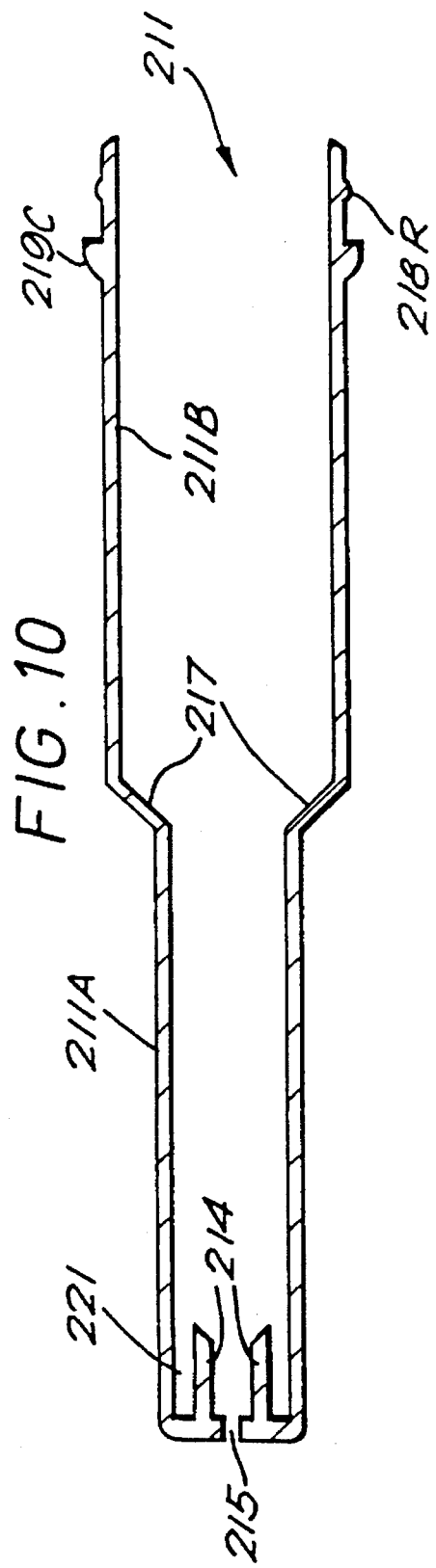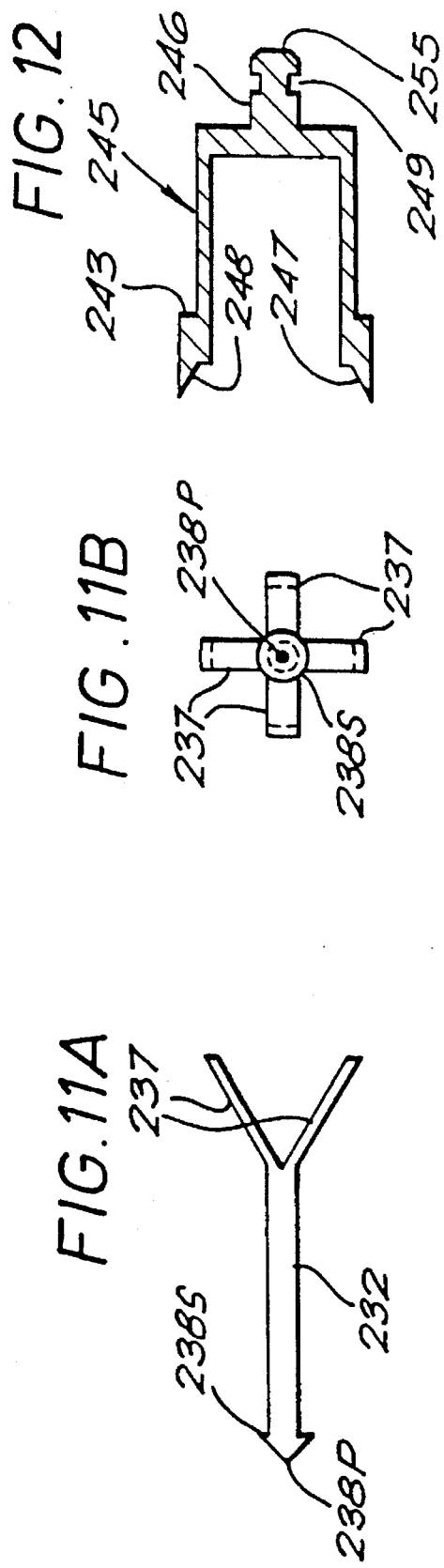

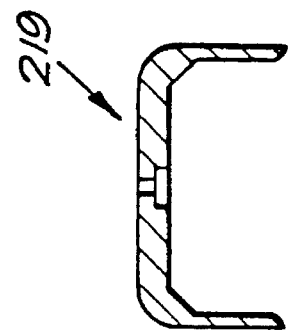
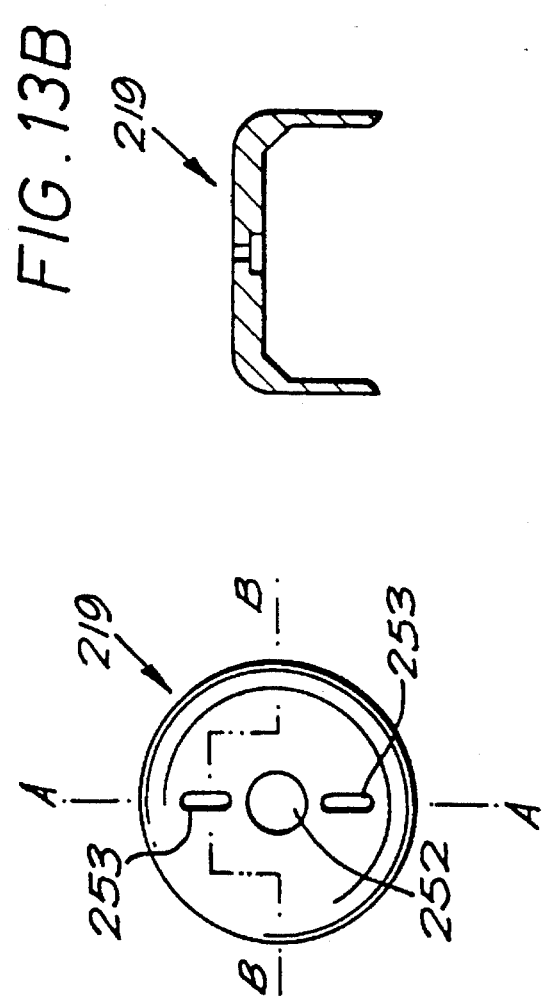
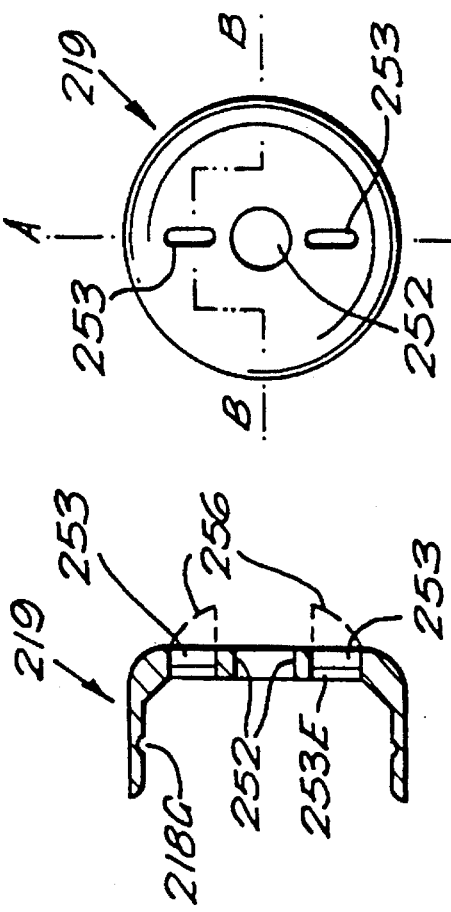
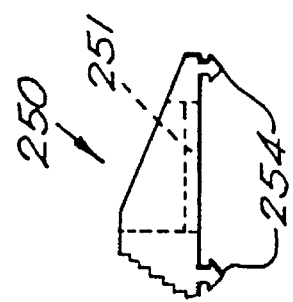
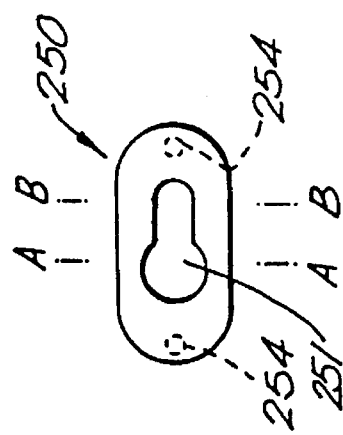
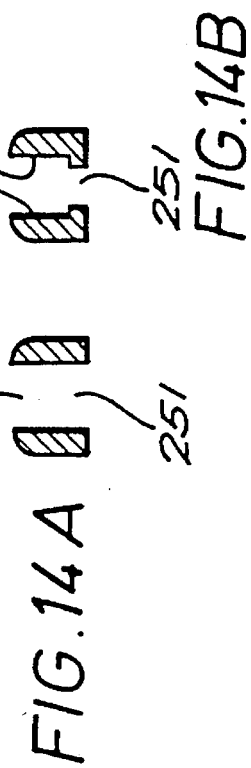

SYRINGE WITH RETRACTABLE NEEDLE

BACKGROUND OF THE INVENTION

This invention relates to hollow needle applicators suitable for administering cartridged drugs etc.

Dangers of infection and cross-infection, much highlighted by the spread of AIDS, mean there is a need for hollow-needle devices as drug etc applicators with automatic retraction and designed for single use only, i.e. designedly not lending themselves to re-use. This is, perhaps, particularly the case for cartridged drugs etc supplied as a one-dose item complete with applicator. Indeed, there have been many proposals over the years for such applicators, especially recently, but most are of doubtful practicality or of complex and costly construction, even both. We have, ourselves, made basic proposals (PCT application GB92/00652) for practical and low-cost single use hypodermic syringes (and body-fluid samplers) with automatic needle retraction, including usable with cartridged drugs etc, but not particularly complete pre-loaded applicator devices, nor with self-powering provision also affording automatic needle extension before cartridge discharge and needle retraction.

SUMMARY OF THE INVENTION

It is a general object of this invention to make further proposals for pre-loaded drugs etc applicators also having potential for practical and low-cost implementation.

In using the term "drug etc" herein, there is no intention to limit application of this invention to drugs as such, even to antidote substances. This invention is seen as generally applicable to any usefully injectable substance; and to doing so into any appropriate receiver, I.e. whether or not that is tissue of a human or even animal subject.

Since filing U.K. Patent Applications from which priority is claimed for the present patent application, we have become aware of a European Patent Application published on 2nd Dec. 1992 under the serial number 0516473. The latter concerns a proposed self-powered cartridged drug etc applicator with automatic sequential needle extension, cartridge contents expression, and needle retraction. An outer body accommodates a drug etc cartridge with a hollow needle within one end of the outer body and extensible therethrough when retraction bias acting on an outwardly flared rearward mouth of the cartridge is overcome. Within the other end of the outer body is a piston actuator and associated power drive spring with a twist then press down arrangement for selectively releasing and power driving the piston actuator to overcome the retraction bias in causing needle extension and cartridge contents expression.

Coupling between the piston actuator and discharge piston of the cartridge is by a piston rod carrying the cartridge piston at one end, and (in the main embodiment) having slotting at its other end further provided with first outwardly extending projections preventing entry of the piston rod into a bore of the piston actuator. Spaced second outwardly extending projections can enter the cartridge at the end of contents expression with the intention of squeezing together the piston rod parts flanking the slotting to allow the slotted end of the piston rod to enter the piston actuator bore. Particular reliance is placed on providing two spaced internal ledgings of the outer body, which, together with specific spacer elements, serve to limit movement of the cartridge and the piston actuator.

Amongst perceived disadvantages of the applicator of EPA 0516473 is manifest requirement for its outer body to be fabricated from separately made components, at least in order to provide the required spaced internal ledgings. Also, illustrated piston rod slotting affords little leverage for the second outwardly extending projections in squeezing together the piston rod parts flanking the slotting; and there is clearly limited entry of a short portion only of the piston rod into the piston actuator bore, actually much less than the lengths of the slotting and the piston rod parts flanking the slotting. The latter effectively defines retraction thus exposable extent of the hollow needle, and further contributes to determining a minimum applicator length much greater than the cartridge-with-needle plus the extended power drive spring. Indeed, complex alternative toggle linkage and displaceable ball release arrangements are described, but appear to be of dubious practicality.

It is a particular object of one aspect of this invention to improve upon at least either or both of those disadvantages, preferably further with simplicity leading to reduced componentry and manufacture/assembly costs, even as applied to self-powered applicators having a "snake's-tongue" action.

According to that aspect of this invention, there is provided a hollow needle applicator for cartridged drugs etc and with automatic needle retraction after cartridge contents expression, wherein its drug etc cartridge can itself be at least partially accommodated bodily within a hollow piston actuator or carrier and will be released for retraction under bias thereinto or further thereinto by way of a piston rod serving to operate contents discharge piston provision of the cartridge and further having deflectable arms that extend sideways further than side walling of the cartridge and into temporary latching engagement with holding formations of the piston actuator or carrier until released by deflection of the arms by engagement with open rear end of the cartridge. Preferred deflectable arms are angled both outwards and away from the cartridge, typically as extensions splayed from end of said piston rod.

Once the arms are so deflected for release purposes, they and the cartridge can travel into the hollow piston actuator or carrier to any desired or permitted extent consistent with satisfactory operation, typically, and with advantage, to an extent greater than the lengths of the arms.

This aspect of invention has application generally to cartridged drug etc applicators with automatic needle retraction, regardless of whether or not self-powering is provided for needle extension and cartridge contents discharge. Typically, a manually operated cartridged drug etc applicator will have a cartridge-accommodating operating plunger entrant an outer body part with its said holding formations medially of its internal extent between its operating end pusher provision and retraction bias release latching provision at its other end, advantageously of internal integrally formed type for a unitarily mouldable said outer body part, say as in our above-mentioned PCT application (GB/92/00652). Also typically, a self-powered cartridged drug etc applicator further affording automatic needle extension and cartridge contents expression can have said holding formations at a mouth of its piston actuator or carrier inside outer extent and action of its power drive provision, then within extended state of which an inner end of the retracted cartridge will come to rest.

For self-powered drug etc applicators, preferred operation involves an as-supplied state in which retraction bias holds its hollow needle withdrawn, say by a partially extended compression spring acting either on a drug etc cartridge with integral or attached said needle or on a separate holder for said needle; and in which power drive provision is held in a powered state, say with full permitted compression of another compression spring acting for power driving purposes on the cartridge piston carrier or actuator.

Preferred cartridge and piston provision involves its drug etc load or contents, usually liquid, being between its piston and a seal penetrable by its needle but holding an hydraulic lock until so penetrated, so that the cartridge and piston provision moves as a whole until the seal is penetrated by the needle. Continued movement of the needle, whether to penetrate clothing as well as tissue or just tissue (or otherwise to enter a receiver), is readily assured, whether as a part of the cartridge or by engagement of the cartridge with needle holder provision.

A suitable seal provision is by a block of sealing material partially penetrated by the needle before getting power driven, but requiring significant needle movement for complete penetration. Such a block may be additional to septum seal provision for the cartridge, even for the outer body itself at its needle exit; and can usefully serve in absorbing shocks, particularly for a glass-bodied cartridge.

A suitable outer body component can be generally tubular and of only progressively different section, preferably internal diameters, larger where housing the power drive and through required movement of parts thereof, smaller where housing retraction bias spring provision and allowing outward and contents expression movement of the needle and cartridge provision, and could be smallest at needle exit, but an internal return about retraction bias spring seating/accommodation is preferred. Transition between largest and smaller parts can serve as the only required internal abutment for power drive operation (to limit movement of the piston carrier or actuator) followed by cartridge and needle retraction. Such an outer body component is readily moulded in one piece, including preferred internal return at needle exit/retraction spring seating/accommodation.

It is particularly preferred that operation to release the power drive provision be other than by way of a push or press action at the opposite end of the actuator to the needle. Specifically, it is preferred that a slide action be used, which can conveniently involve an end cap for the outer body component, the end cap having an exterior slide with a projection through to an end enlargement or knob cooperating with a key-hole like slot in end of the piston carrier or actuator.

For a normally manually operated cartridged drug etc applicator, another aspect of this invention provides that a plunger serve to accommodate a drug etc cartridge coupled to a hollow discharge needle and as driven back into the applicator with the cartridge after discharge of the cartridge and release of internal latching means of the applicator, preferably formed integral with and inside its outer body.

In a further aspect of this invention, a drug etc applicator hereof has a biassed needle holder that is formed separately from a drug etc cartridge and held by internal latching until released by a plunger, the needle holder having capture formations for coupling to the cartridge in order for its needle to pierce the cartridge. There can be sufficient play in the coupling between the needle holder and the cartridge for the latter to have its discharge seal pierced only after coupling between them is achieved and is not reversible within a cylindrical outer body of the applicator. A suitable coupling between the needle holder and the cartridge is of snap-fitting type. One practical embodiment comprises an exteriorly rimmed formation protruding from the needle holder and inwardly formed teeth on extensions at the end of the cartridge.

In one embodiment, cartridge capture formation of the needle holder is within and spaced inwardly from needle holder latching formations of the applicator's outer body component. A preferred plunger fits between the applicator's outer body component and the cartridge, or at least plunger formations to release internal needle holder latching of the outer body component do so.

BRIEF DESCRIPTION OF THE DRAWINGS

Exemplary specific implementation for this invention will now be described with reference to the accompanying drawings, in which:

FIG. 1 is a side sectional view of a manually operated applicator hereof before use to discharge a cartridge;

FIG. 2 is a side sectional view of the same applicator showing fitting of a cartridge;

FIG. 3 is a side sectional view of the same applicator part-way through discharging the cartridge;

FIG. 4 is a side sectional view of the same applicator with its needle and the cartridge withdrawn automatically after use;

FIGS. 5 to 8 are longitudinal sections showing states and stages of operation for a self-powered applicator embodiment.;

FIG. 9 is a fragmentary longitudinal section showing an alternative with a hollow needle and holder separate from a drug etc cartridge; and FIGS. 10; 11A,B; 12; 13A–C; 14A–D show details of moulded component parts, in various side, plan and section views, for a particular preferred self-powered applicator.

DESCRIPTION

In FIGS. 1 to 4, the applicator comprises an outer cylindrical, normally circular section, outer body part 10 having successive reductions to a forward chamber 12 and an exit passage 14 therefrom for a hollow needle 20. The outer body part has internal latching formations that extend at 16 from first reduction of the body part 10 and have inwardly extending slope-faced teeth 18. The latching formations 16,18 are spaced from the interior of the body part 10, at least, indeed preferably only, locally at each of the latching formations 16,18 so they can flex radially outwardly. The forward chamber 12 houses a compressed drive spring 22 bearing on a needle holder 24 carrying the needle 20. The needle holder 24 is shown in FIG. 1 captured by the teeth 18 of the latching formations. Sloping faces 26 of the latching teeth 18 are engagable for release by sloping end 28 of a hollow piston actuator or carrier (specifically for temporarily carrying a piston rod of or for the cartridge piston) in the form of a plunger 30.

The outer body part 10 is similar to that of our above-mentioned PCT application, including end grip flanging 27 and capture recessing 29 for the plunger 30, and except for omitting seals between the needle holder 24 and entry to the forward chamber 12 and at the end of the forward chamber 12. As with our copending PCT application, the outer body part 10 is mouldable in a single piece.

The plunger 30 also has substantial similarity to those of our above-mentioned PCT application; but with extra length, basically at 32 between its capture formations 34 and its end flanging 36, and inner temporary capture recessing 38 for extension arms 42 of a cartridge piston rod 40. No rupturable inward end closure is shown for the plunger, and it could have slots in its seal rim 39, but may well not need them if there are no seals to the needle 20 and the needle holder 24 in and at the forward chamber 12.

The needle holder 24 is also similar to that of our copending PCT application, save for not requiring any sealing, and having capture formations 44 extending inwardly therefrom in defining a recess 45 below an undercut rim 46. The needle 20 is sharp at both ends and extends beyond the capture formations 44.

The cartridge piston rod 40 has an enlarged or otherwise appropriately formed end 48 by which it press-fits into a piston 52 of cartridge 50, see recess 54 in the piston 52. The splayed arms 42 of the piston rod 42 diverge away from its end furthest within the plunger 30, and engage the recessing 38 so as to travel with the plunger 30 and resist substantial force (adequate to discharge the cartridge 50) until released from the recessing 38, preferably positively by end 56 of the cartridge 50 (as will be described).

At its other end, the cartridge 50 has a septum seal 58 held in a conventional formation 60 (not shown accurately) and extensions 62 beyond the septum seal. The extensions 62 go to undercut teeth formations 64 and are deflectable in order to engage over the undercut rim 44 of the needle holder 24. Once so engaged, the teeth formations 64 cannot be disengaged from within the body part 10.

It is feasible, though not so shown in the drawings, and can be advantageous, for the cartridge's septum seal 58 not to be pierced (or fully pierced) until after the teeth formations 64 engage in the needle holder extension recess 45. Indeed, if that recess 45 is of sufficient length axially of the applicator, it is possible to ensure that the septum seal 54 is not pierced unless the cartridge 50 is forced down on the needle holder 24 (as can be assured by friction between the cartridge 50 and its piston 52 or simply relying on hydraulic lock by contacts of the cartridge unless the needle 20 pierces the septum seal 58).

It will be appreciated that the manually-operated applicator of FIGS. 1 to 4 can be supplied sterile and could be so supplied with its outer body part 10 and its plunger 30 separate rather than the latter inserted into the former as shown in FIG. 1. In any event, the outer body part 10 is free of the plunger 30 when loaded with a cartridge 50, see FIG. 2. The piston rod 40 for the cartridge 50 might often, if not mostly, supplied separately from the cartridge 50 itself, though usually in the same sterile blister pack (as for supply of the outer body part 10 and plunger 30). That is possible for use with the illustrated manually operated applicator. Indeed, the piston rod 40 could be supplied already mounted in the plunger 30. However, that is not essential, and it may well be preferred, as a matter of practice and practicality, to push-fit the piston rod 40 with the cartridge piston 52 before squeezing the arms 42 and pushing the plunger over them, those arms 42 then inevitably and automatically springing out for engaging the internal recessing 38 of the plunger 30.

Engagement of the arms 42 in the plunger recessing 38 is, of course, essential for the illustrated applicator to discharge the cartridge 50 through the needle 20 by movement of the plunger 30, see FIG. 3. At full discharge of the cartridge 50, the plunger 30 will release the latching formations 16,18. At the same time, or just prior thereto, the end rim 56 of the cartridge 50 can release the arms 42 of the piston rod 40 out of the internal plunger recessing 38. Alternatively, the force of the spring 22 when released by the latching formations 16,18 may be sufficient to ensure disengagement of piston rod arms 42 from the internal plunger recessing 38, say still using the end rim 56 of the cartridge 50. The result of such inward movement of the arms 42 is shown in FIG. 4, where the arms are within the end rim 56 of the cartridge 50, and the whole of the needle 20 as well as the cartridge 50 is irretrievably driven within the applicator body part 10 and extension 32 of the plunger 30.

It will be appreciated that only quite minor modifications or changes are required to the applicator of our copending PCT application and to conventional drug cartridges in order to practice this invention.

One alternative variant not illustrated would be for the plunger 30 to be in two parts, the outermost one of which could have a rupturable closure; and for the piston end of the cartridge to have rupture formations. Then, the rupturable closure could act directly on the end of a standard cartridge piston rod (or specially sized and configured end if more appropriate), and there would be rupture when required, perhaps preferably at or just before release of the latching members (16,18). The two required plunger parts could, if desired, simply push fit together in socket and hollow spigot fashion.

Turning to FIGS. 5 to 8, an illustrated self-powered applicator 110 has an outer body component 111 that is generally tubular with parts 111A,B of different section, one smaller than the other. The smaller section part 111A extends from one end 113A, that is shown with internally returned necking 114 and orificed at 115 for passing a hollow needle 120, to a shoulder 117. The larger section part 111B extends from the other end 113B to the shoulder 117, and has an end cap 119 shown snap-fitting by rib and groove formations 118R,G.

The sectional view of FIG. 10 shows all aforesaid features of an outer body component referenced 211 (and with other equivalent references advanced by 100), and differing from that of FIGS. 5 to 8 only by showing an outward end-cap stop formation 219C. Such outer body parts 111,211 are readily injection moulded in one piece Reverting to FIGS. 5 to 8, the smaller section body part 111A affords an annular seating recess 121 for a retraction bias spring 123 shown acting on a cartridge 125 provided with an integral or secured-in hollow needle 120. The needle 120 is shown in FIG. 5 extending within helical retraction spring 123 to and partially penetrating a block 126 of sealing material that may be readily deformable and is shown seated in a recess 127 within annular wall 114 bounding the annular retraction spring seating recess 121 and from which the needle passing orifice 115 extends.

The cartridge 125 has a piston 130 by which its contents (see volume referenced 133 of FIGS. 5 and 6) can be pressed through the needle 120 after its full penetration of the sealing block 126, shown in FIG. 6 as involving compressive deformation. The piston 130 has a piston rod 132 of a length substantially corresponding to the discharge stroke of the piston 130, i.e. to the volume 133, at least when taking into account engagement of end 135 of the cartridge with angled piston extension arms 137 going outwards beyond the outer confines of the cartridge 125 and serving to move same inwardly for purposes to be described.

FIGS. 11A,B show full details of a particular piston rod 232, which can conveniently be of generally circular section apart from its extension arms 237. Four splayed extension arms 237 are shown equally spaced and can be of slightly arcuate section. Also, a pointed and shouldered snap-in formation is shown at 238P,238S for attachment to the piston 130, into correspondingly shaped recessing of the latter.

Returning to FIGS. 5 to 8, the larger section body part 111B houses a power drive spring 141 acting between the end cap 119 and exterior shoulder 143 of a cartridge piston carrier or actuator 145 that is shown hollow and capable of accepting the angled piston extension arms 137 when they are sufficiently squeezed inwards. However, open end 146 of the piston rod carrier or actuator 145 is shown with a ledge formation 147 to engage ends of the piston extension arms 137 and a taper 148 into that ledge 147.

Closed end 149 of the piston carrier or actuator 145 is shown with a slot 151 that will be of a key-hole shape to allow capture and release of the piston carrier or actuator 145 according to the position of a slide 150 operable in a registering slot 153 in the end cap 119 and having a capture/release knob 155 for the piston carrier or actuator 145.

FIG. 12 is a section through a particular piston carrier or actuator 245 with outer power spring seating shoulder 243, ledging temporarily to hold the piston rod extension arms 237, and taper 248 thereto. In addition, its closed end 249 is not slotted, but instead carries an outwardly extending integrally formed post 246 that is circumferentially reduced at 248 before an end knob 255.

FIGS. 13A,B,C are A—A, B—B section and plan views of a particular end cap 219 with internal snap-fit grooving 218G, but otherwise modified compared with end cap 119. Specifically, a central hole 252 allows passage therethrough of the post 246, particularly its end knob formation 255. To each side of the hole 252 are aligned elongated slots 253 internally extended (253E) for capture and relative sliding of arrow-head section spigots 254 protruding from the bottom of particular slider 250 of FIGS. 14A-D that is preferably a slide fit also between external protrusions that are shown dashed only at 256 in FIG. 13A. That slider 250 is shown by way of A—A, B—B sections, bottom plan and side views, respectively, in FIGS. 15A,B,C,D, and has slotting including a lower key-hole slot 251 below an accommodation slot 251A for the knob 255 generally within the height of the slider 250. The slider 250, cap 219 and piston carrier/actuator post 246 and knob 255 serve a generally equivalent functional purpose to the power drive release arrangement of FIGS. 5 to 8, to which description now reverts.

In its as-supplied state, see FIG. 5, the device 110 has the piston carrier or actuator 145 captive to the end cap 119 so that the power drive spring 141 is compressed; and the retraction spring 121 is partially extended to hold the cartridge 125 firmly located with the piston rod extension arms 137 seated at the ledge formation 147, at least for liquid contents of the cartridge effectively affording an hydraulic lock. The needle 120 is wholly retracted within the body part 111A.

Releasing the piston rod carrier or actuator 145, by operating the slide 150, allows the power drive spring 141 first to move the cartridge 125, thus force the needle 120 through the sealing block 126 and out of the orifice 119, at the same time compressing the retraction spring 123, ultimately also the sealing block 126 if deformable, see FIG. 6; then to express the contents of the cartridge 125 through the extended needle 120, see FIG. 7; and finally to engage (see also FIG. 7) the end 135 of the cartridge 125 on the piston rod extension arms 137 so as to squeeze them together and out of the ledge formation 147.

FIG. 7 actually shows the sealing block 126 without deformation, and that may be its nature; or it may recover after deformation, once the contents of the cartridge 125 can escape through the needle 120, and with some recovery of the retraction spring 121 also indicated—but not enough to interfere with desired operation (otherwise it would, of course be prevented by design).

Thereafter the piston rod carrier or actuator 145 is arrested by the shoulder 117, and the retraction spring 121 extends in driving the cartridge 125 (complete with needle 120 and piston 130, piston rod 132 and extension arms 137) rearwardly, see FIG. 8, into the smaller body part 111A and the interior of the piston rod carrier or actuator 145 and through into the forward part of the larger section body part 111B.

A septum disc seal 160 is shown in the needle passing orifice 115, and can serve advantageously in securing a completely safe disposable item after use (as in FIG. 8).

The alternative embodiment of FIG. 9 has a modified nose formation of the smaller body part 111A, basically to serve only in seating the retraction spring 121 and affording needle passage at 115 in its thicker neck wall 123'. The hollow needle 120' is in a holder 120H acted upon by the retraction spring 121; and sealing block 126' is shown at the inner end of the needle 120', actually against another septum disc seal 162 for the end of the cartridge 125' (substantially as has been normal hitherto). General equivalence of operation effectiveness should readily be appreciated.

For all illustrated embodiments, it will be clear that the piston rod extension arms 42, 137 and 237 are—for release from the piston carrier or actuator 40, 145, 245 to assure needle retraction—engaged by the end of the cartridge concerned (50, 125) at outermost limits of the latter, thus with maximum leverage for release purposes. Moreover, angling of the arms extending away from the piston rod substantially assists providing required stiffness for at least cartridge contents expression in contrast to also required deflectability for release purposes. Arcing of the sections of the arms (as for those 237) can also further assist in these respects. Clearly, there is no limitation placed by those arms on the extent to which retraction takes place into the piston actuator, and the cartridge itself normally and preferably so enters the piston actuator.

I claim:

1. A hollow needle applicator for cartridged drugs etc. including automatic needle retraction after cartridge contents expression, said applicator comprising a cartridge which is at least partially accommodated bodily within a hollow piston actuator or carrier and will be released for retraction under bias thereinto or further thereinto by way of a piston rod serving to operate contents discharge piston provision of said cartridge and said piston further having deflectable arms that extend sideways further than side walling of said cartridge and into temporary latching engagement with holding formation of said piston actuator or carrier until released by deflection of the arms by engagement with open rear end of said cartridge.

2. Applicator as claimed in claim 1, wherein the deflectable arms are angled both outwards and away from the cartridge.

3. Applicator as claimed in claim 2, wherein the deflectable arms comprise extensions splayed from end of said piston rod free of coupling to the cartridge piston.

4. Applicator as claimed in claim 1, wherein retraction of the cartridge into the piston carrier or actuator is to a greater extent than lengths of the arms.

5. Applicator as claimed in claim 1 and for manual operation, wherein the piston carrier or actuator comprises a cartridge-accommodating plunger slidable within an outer body part with its said holding formation medially of its internal extent between operating end pusher provision and retraction bias release latching provision at its other end internally of the outer body.

6. Applicator as claimed in claim 5, wherein a needle holder formed separately from the cartridge carries a needle for piercing the cartridge in order to discharge cartridge contents, the needle holder having capture formations for coupling to the cartridge for such piercing.

7. Applicator as claimed in claim 6, wherein the capture formations permit sufficient play between the needle and the cartridge for complete piercing of discharge sealing of the cartridge only after the coupling is achieved between the cartridge and the needle holder.

8. Applicator as claimed in claim 6, wherein the needle holder has an exteriorly rimmed formation extending therefrom and the cartridge has inwardly formed teeth on extensions from the cartridge to snap-fit to the exterior rimmed formation (47).

9. Applicator as claimed in claim 6, wherein the capture formations of the needle holder are spaced inwardly of said bias release latching formations operative relative to the needle holder and formed integrally with the outer body, and the plunger fits between the cartridge and the outer body.

10. Applicator as claimed in claim 1, and for self-powered operation further affording automatic needle extension and cartridge contents expression before automatic needle retraction, wherein said holding formations are at a mouth of the piston carrier or actuator which is disposed within an outer body part and inside outer extent and action of power drive provisions.

11. Applicator as claimed in claim 10, wherein retraction of the cartridge results in the cartridge extending to some extent within the power drive provisions in the extended state of those power drive provisions.

12. Applicator as claimed in claim 10, wherein the outer body part has only progressively different internal sections, larger where the housing power drive provisions and through required movement of parts thereof, and smaller where housing the retraction bias provision and allowing outward and contents expression movement of the needle and the cartridge.

13. Applicator as claimed in claim 12, wherein transition from the larger to the smaller section serves as the only required internal abutment for power drive operation followed by cartridge and needle retraction.

14. Applicator as claimed in claim 11, wherein exit from the outer body for the needle is through a re-entrant internal necking formation spaced from said smaller section to afford seating accommodation for a spring providing the retraction bias.

15. Applicator as claimed in claim 10, wherein a seal provision requiring to be penetrated by the needle comprises a block of sealing material partially penetrated by the needle comprises a block of sealing material partially penetrated by the needle before getting power driven, but requiring significant movement of the needle for complete penetration.

16. Applicator as claimed in claim 10, wherein means for releasing power drive and operating the applicator includes slide-action provision at the opposite end of the applicator to the needle.

* * * * *